(12) United States Patent
Cicenas et al.

(10) Patent No.: US 7,351,210 B2
(45) Date of Patent: Apr. 1, 2008

(54) BIOPSY DEVICE WITH PISTON ADVANCE

(75) Inventors: Chris Cicenas, Columbus, OH (US); Luke Stonis, Columbus, OH (US)

(73) Assignee: Ethicon-Endo-Surgery, Inc., Cincinatti, OH (US)

( * ) Notice: Subject to any disclaimer, the term of this patent is extended or adjusted under 35 U.S.C. 154(b) by 275 days.

(21) Appl. No.: 10/732,848

(22) Filed: Dec. 10, 2003

(65) Prior Publication Data
US 2005/0101880 A1 May 12, 2005

Related U.S. Application Data

(60) Provisional application No. 60/432,545, filed on Dec. 11, 2002.

(51) Int. Cl.
 *A61B 10/00* (2006.01)
(52) U.S. Cl. .............. 600/564; 600/565; 600/566; 600/567; 600/568; 600/562
(58) Field of Classification Search ........... 600/564, 600/565, 566, 567
See application file for complete search history.

(56) References Cited

U.S. PATENT DOCUMENTS 4,662,869 A * 5/1987 Wright ................. 604/22
5,526,822 A 6/1996 Burbank et al.
5,649,547 A 7/1997 Ritchart et al.
5,769,086 A 6/1998 Ritchart et al.
5,775,333 A 7/1998 Burbank et al.
5,928,164 A 7/1999 Burbank et al.
5,964,716 A 10/1999 Gregoire et al.
5,980,469 A 11/1999 Burbank et al.
6,007,497 A 12/1999 Huitema
6,017,316 A 1/2000 Ritchart et al.
6,077,230 A 6/2000 Gregoire et al.
6,086,544 A 7/2000 Hibner et al.
6,120,462 A * 9/2000 Hibner et al. ............. 600/566
6,228,055 B1 5/2001 Foerster et al.
6,231,522 B1 5/2001 Voegele et al.
6,273,862 B1 8/2001 Privitera et al.
6,638,235 B2 * 10/2003 Miller et al. ............. 600/566
6,712,773 B1 3/2004 Viola
6,758,824 B1 * 7/2004 Miller et al. ............. 600/568
2001/0007925 A1 * 7/2001 Ritchart et al. ............ 600/567
2002/0016555 A1 * 2/2002 Ritchart et al. ............ 600/567
2002/0082519 A1 6/2002 Miller et al.
2003/0199753 A1 10/2003 Hibner et al.

* cited by examiner

*Primary Examiner*—Max F. Hindenburg
*Assistant Examiner*—H. Q. Nguyen
(74) *Attorney, Agent, or Firm*—Gerry S. Gressel (57) ABSTRACT

A biopsy device is provided. The biopsy device can include a cutter which is advanced through a first portion of its stroke by a differential fluid pressure acting on a piston. A mechanical drive can be used to translate and rotate the cutter during tissue severing.

19 Claims, 13 Drawing Sheets

BIOPSY DEVICE WITH PISTON ADVANCE

This application claims priority to provisional patent application 60/432,545 filed Dec. 11, 2002.

This application cross references and incorporates by reference U.S. Patent Application "Biopsy Device With Sample Tube" filed on even date herewith in the names of Cicenas et al.

FIELD OF THE INVENTION

The present invention relates in general to biopsy devices and more particularly to methods and devices for advancing and driving a cutter in a biopsy device.

BACKGROUND OF THE INVENTION

The diagnosis and treatment of patients with cancerous tumors is an ongoing area of investigation. Medical devices for obtaining tissue samples for subsequent sampling are known in the art. For instance, a biopsy instrument now marketed under the tradename MAMMOTOME is commercially available for use in obtaining breast biopsy samples.

Various imaging techniques including X-ray, MRI, CT, and ultrasound imaging may be used with biopsy devices for use in acquiring one or more tissue samples. It can be desirable to use an image guided, percutaneous biopsy instrument which is vacuum assisted, such as the MAMMOTOME device, to acquire multiple tissue samples without removing a biopsy needle between samples.

The following patent documents disclose various biopsy devices and are incorporated herein by reference in their entirety: U.S. Pat. No. 6,273,862 issued Aug. 14, 2001; U.S. Pat. No. 6,231,522 issued May 15, 2001; U.S. Pat. No. 6,228,055 issued May 8, 2001; U.S. Pat. No. 6,120,462 issued Sep. 19, 2000; U.S. Pat. No. 6,086,544 issued Jul. 11, 2000; U.S. Pat. No. 6,077,230 issued Jun. 20, 2000; U.S. Pat. No. 6,017,316 issued Jan. 25, 2000; U.S. Pat. No. 6,007,497 issued Dec. 28, 1999; U.S. Pat. No. 5,980,469 issued Nov. 9, 1999; U.S. Pat. No. 5,964,716 issued Oct. 12, 1999; U.S. Pat. No. 5,928,164 issued Jul. 27, 1999; U.S. Pat. No. 5,775,333 issued Jul. 7, 1998; U.S. Pat. No. 5,769,086 issued Jun. 23, 1998; U.S. Pat. No. 5,649,547 issued Jul. 22, 1997; U.S. Pat. No. 5,526,822 issued Jun. 18, 1996; U.S. Patent Publication 2003/0199753 published Oct. 23, 2003 by Hibner et al.

BRIEF SUMMARY OF THE INVENTION

The invention provides an apparatus and method useful for obtaining a biopsy sample. The apparatus can be used to advance a hollow cutter at a relatively rapid speed to a first position, and then advance the cutter at a relatively slower speed while rotating the cutter to sever tissue.

In one embodiment, the invention provides a biopsy device comprising a hollow biopsy needle having a lateral tissue receiving port; a hollow cutter advancable within the biopsy needle; a first mechanism for advancing the cutter to a position proximal of the lateral tissue receiving port; and a second mechanism for advancing the cutter distal of the position proximal of the lateral tissue receiving port. The first mechanism can employ a pressure differential across a piston actuator to advance the cutter. The first mechanism can advance the cutter at a first relatively rapid rate, and the second mechanism can advance the cutter at a second, relatively less rapid rate.

In one embodiment, the present invention provides a hollow biopsy needle having a lateral tissue receiving port; a hollow cutter advancable within the biopsy needle; a first drive for advancing the cutter to a first position within the hollow biopsy needle; and a second drive for advancing the cutter to a second position within the hollow biopsy needle. The first drive can comprise a pneumatic drive, and the second drive can comprise a non-pneumatic drive. The non-pneumatic drive can include a mechanical drive for translating and rotating the cutter during severing of the tissue sample.

The present invention also provides a method for obtaining a biopsy sample comprising providing a hollow biopsy needle having a tissue receiving port; providing a cutter for severing tissue; positioning the needle in a tissue mass; drawing tissue into the tissue receiving port; providing a pressure differential for advancing the cutter within the biopsy needle to a first position proximal of the tissue receiving port; and advancing the cutter without using the pressure differential from the first position proximal of the tissue receiving port to a position distal of the port to sever a tissue sample. The step of advancing the cutter to the first position can comprise pneumatically advancing the cutter.

In one embodiment, a handheld biopsy device is provided having a hybrid pneumatic piston drive and motor drive for advancing a hollow cutter within a biopsy needle having a lateral tissue receiving port. A vacuum source is used to draw tissue into the biopsy needle. A vacuum source, which can be the same source or a different source, can be used to provide distal advancement and proximal retraction of the piston and cutter along a portion of the cutter's axial stroke. The piston drive can be used to advance the cutter to a first position just proximal to the tissue port, and the motor drive can be used to rotate the cutter and translate the cutter past the tissue receiving port to sever tissue.

BRIEF DESCRIPTION OF THE FIGURES

FIG. 5c is a schematic illustration of components of the spool valve assembly.

DETAILED DESCRIPTION OF THE INVENTION

Figure 1:
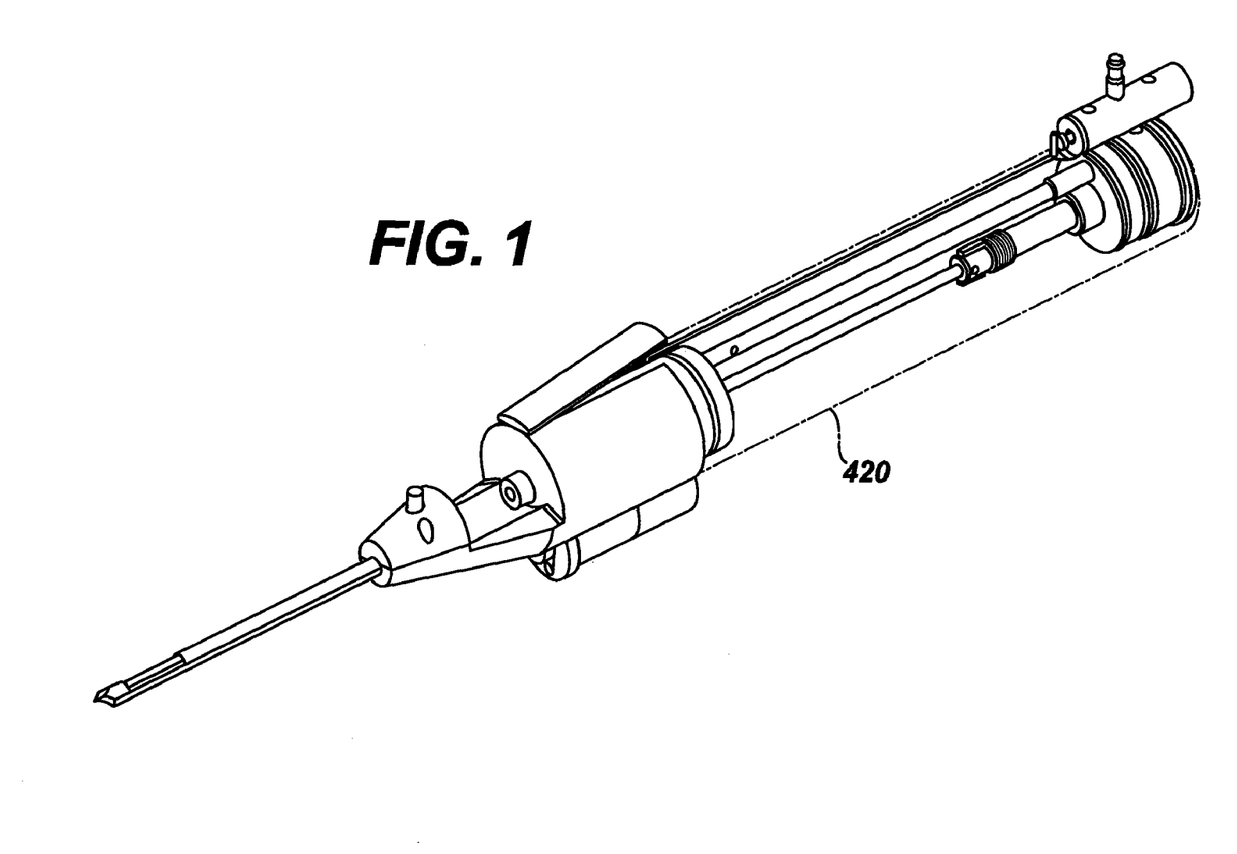
FIG. 1 is a schematic illustration of biopsy device of the present invention.
Figure 1A:
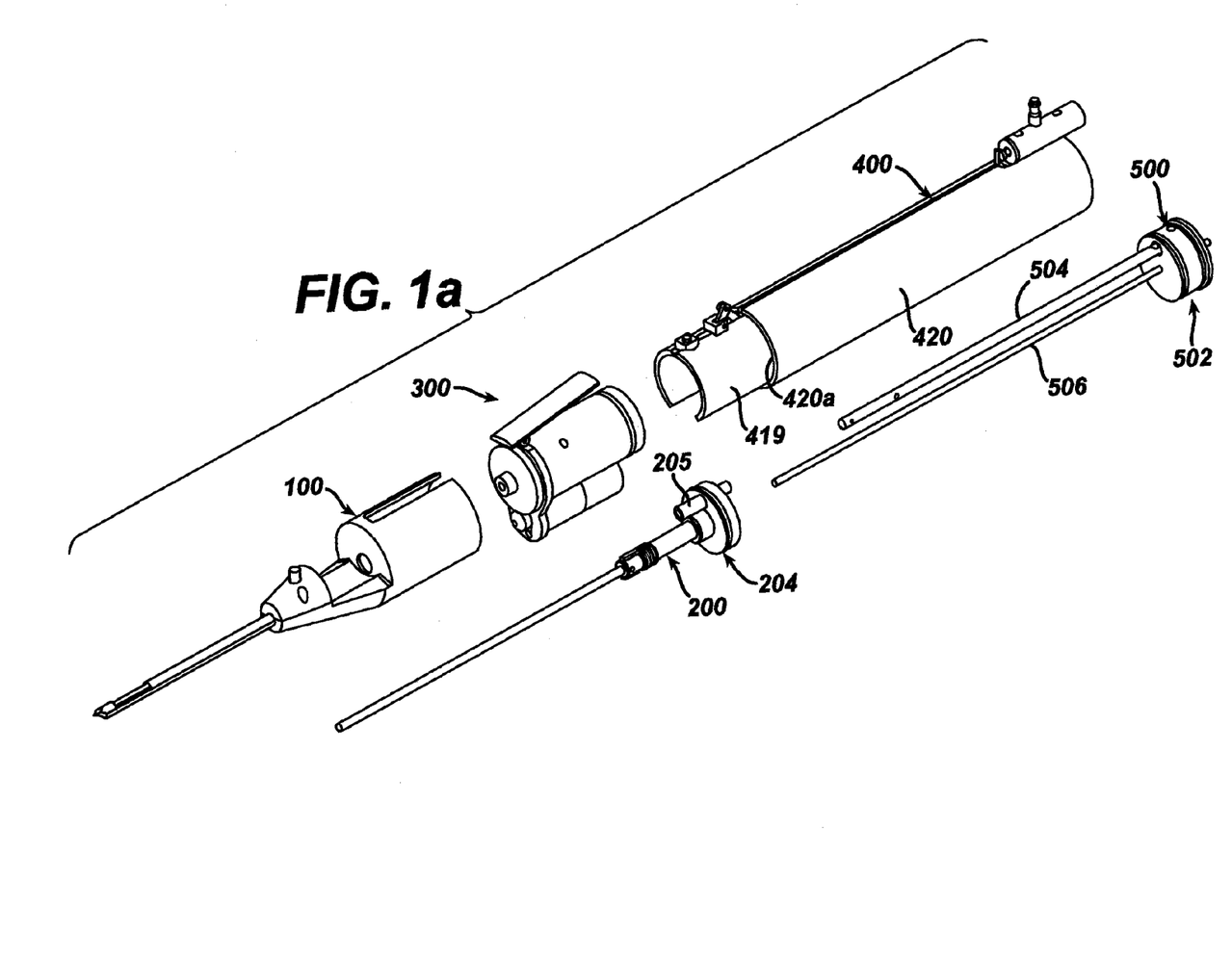
FIG. 1a is a schematic illustration of subassemblies of the biopsy device of FIG. 1.

FIGS. 1 and 1a illustrate a biopsy device according to the present invention. In the embodiment shown in FIGS. 1 and 1a, the biopsy device is shown comprising a needle assembly 100, a piston and cutter assembly 200, a front end cap assembly 300, a cylinder and spool valve assembly 400, and a rear end cap assembly 500.

Overview of Assembly:

The front end cap assembly 300 can fit inside, and be located at the distal end of cylinder and spool valve assembly 400. The needle assembly 100 can be positioned over the distal end of cylinder and spool valve assembly 400. The proximal end of needle assembly 100 can fit over a distal, reduced diameter portion 419 of clear, thin walled tube 420 which extends forward of lip feature 420a of thin-walled tube (420). The three assemblies 100, 300, and 400 can be secured together by any suitable attachment means, such as with screws.

Figure 1B:
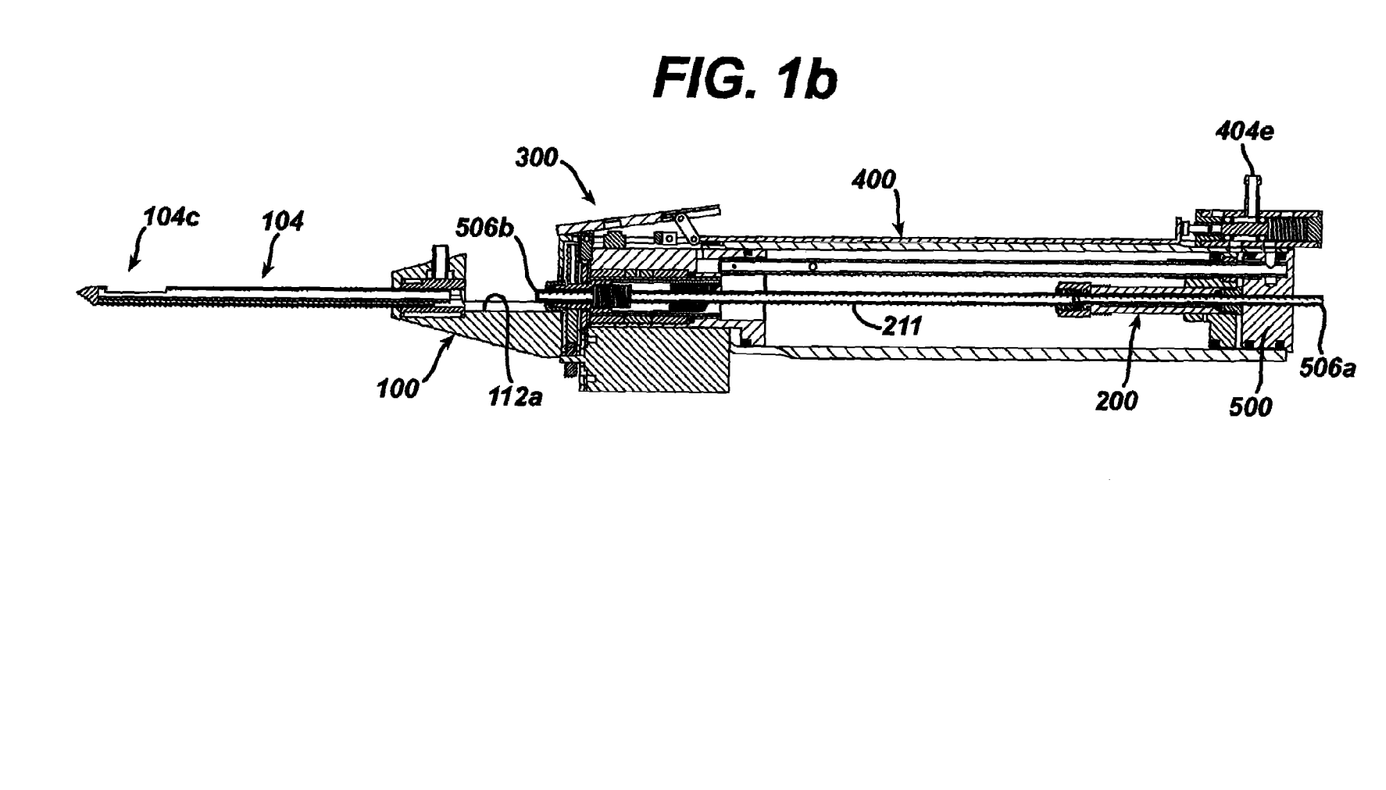
FIG. 1b is a cross-sectional illustration of assembled subassemblies shown in FIG. 1.

The piston and cutter assembly 200 can be slidably disposed inside the tube 420 of the cylinder and spool valve assembly 400, and can be positioned proximal of the front end cap assembly (300). As described in more detail below, the piston can be supported so as not to rotate within the tube 420. Rear end cap assembly 500 fits snugly inside the proximal end of the cylinder and spool valve assembly 400, with guide tube 504 extending into piston guide 205, and knockout tube 506 inserted through the center of piston and cutter assembly 200. The distal end of guide tube 504 is also lightly pressed into a guide tube hole 312b (FIG. 4a) in the proximal face of front end cap assembly 300. FIG. 1b provides a cross-sectional view of the assemblies 100, 200, 300, 400, and 500 assembled together, showing the cutter in it's proximal most position.

Needle Assembly 100

Figure 2:
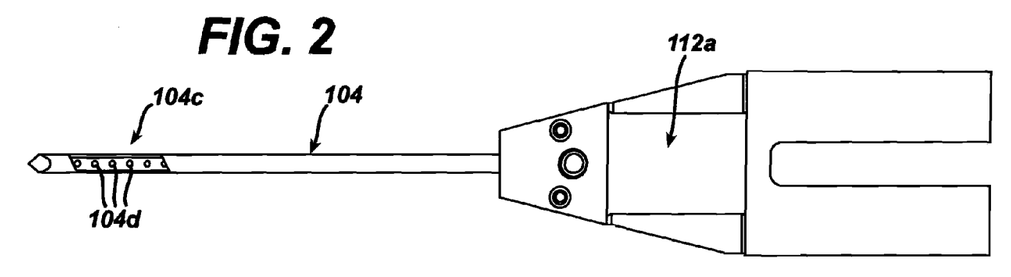
FIG. 2 is a top view schematic illustration of the needle assembly shown in FIG. 1.
Figure 2A:
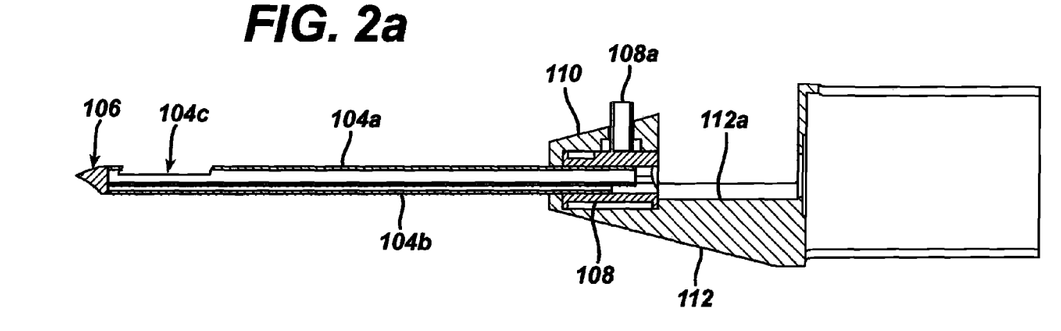
FIG. 2a is a side elevation cross-sectional illustration of the needle assembly in FIG. 2.

Referring to FIG. 2, The needle assembly (100, FIG. 2) can include an elongated, hollow needle 104, a distal tissue piercing needle tip 106, a needle support 108, an upper housing 110, and lower housing 112.

The needle 104 can include an upper cutter lumen 104a, a lower vacuum lumen 104b, and a plurality of interlumen vacuum holes 104d. The needle 104 can also include a lateral tissue receiving port 104c communicating with cutter lumen 104a. The vacuum holes 104d can be positioned below the port 104c and can be used to convey vacuum from the vacuum lumen to assist in drawing tissue into the cutter lumen through the port 104c. The needle tip 106 can be supported on the distal end of needle 104 to be positioned distal of the port 104c, and the tip 106 can close the distal ends of the cutter lumen and the vacuum lumen.

The needle 104 can be fixed, such as by adhesive or other suitable means, to needle support 108. Support 108 can be captured between the upper shell housing 110 and the lower shell housing 112. The upper and lower housings can be attached in any suitable manner, such as with screw fasteners, adhesive, or snap fit features. The lower shell housing 112 can include a generally flat specimen receiving surface 112a positioned proximally of the needle support 108. Tissue specimens received through cutter lumen 104a can be deposited on surface 112a.

A vacuum inlet port 108a can be provided in needle support 108. Vacuum inlet port 108a can be connected to an external source of vacuum (such as vacuum source 600 in FIG. 7). Vacuum can be communicated to lateral tissue receiving port 104c via inlet port 108a, which communicates with lower lumen 104b, which in turn communicates with lateral vacuum holes 104d positioned below the port 104c, as illustrated schematically in FIG. 7.

Piston and Cutter Assembly 200

Figure 3:
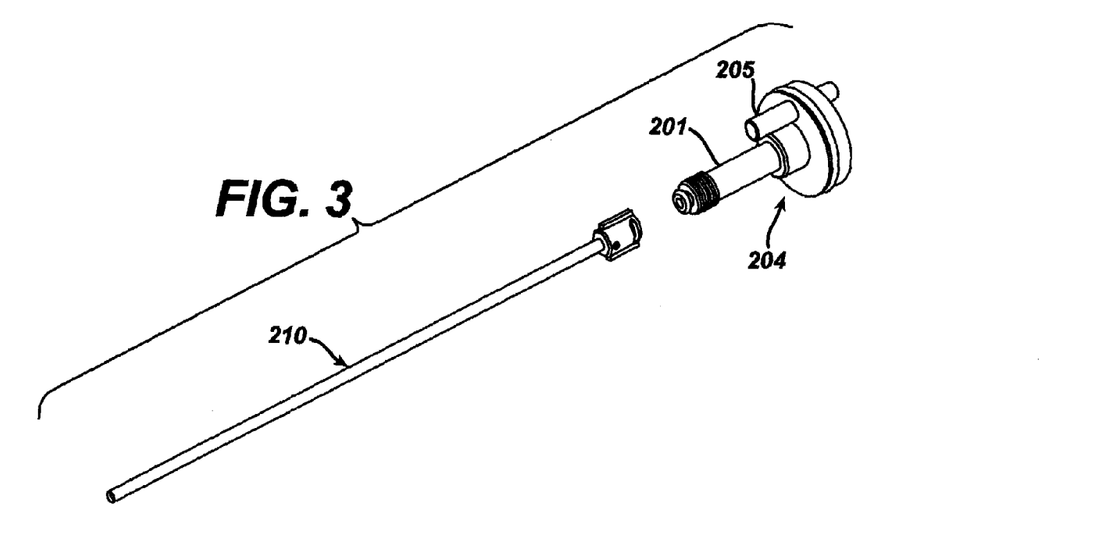
FIG. 3 shows the piston assembly separated from the cutter assembly.
Figure 3A:
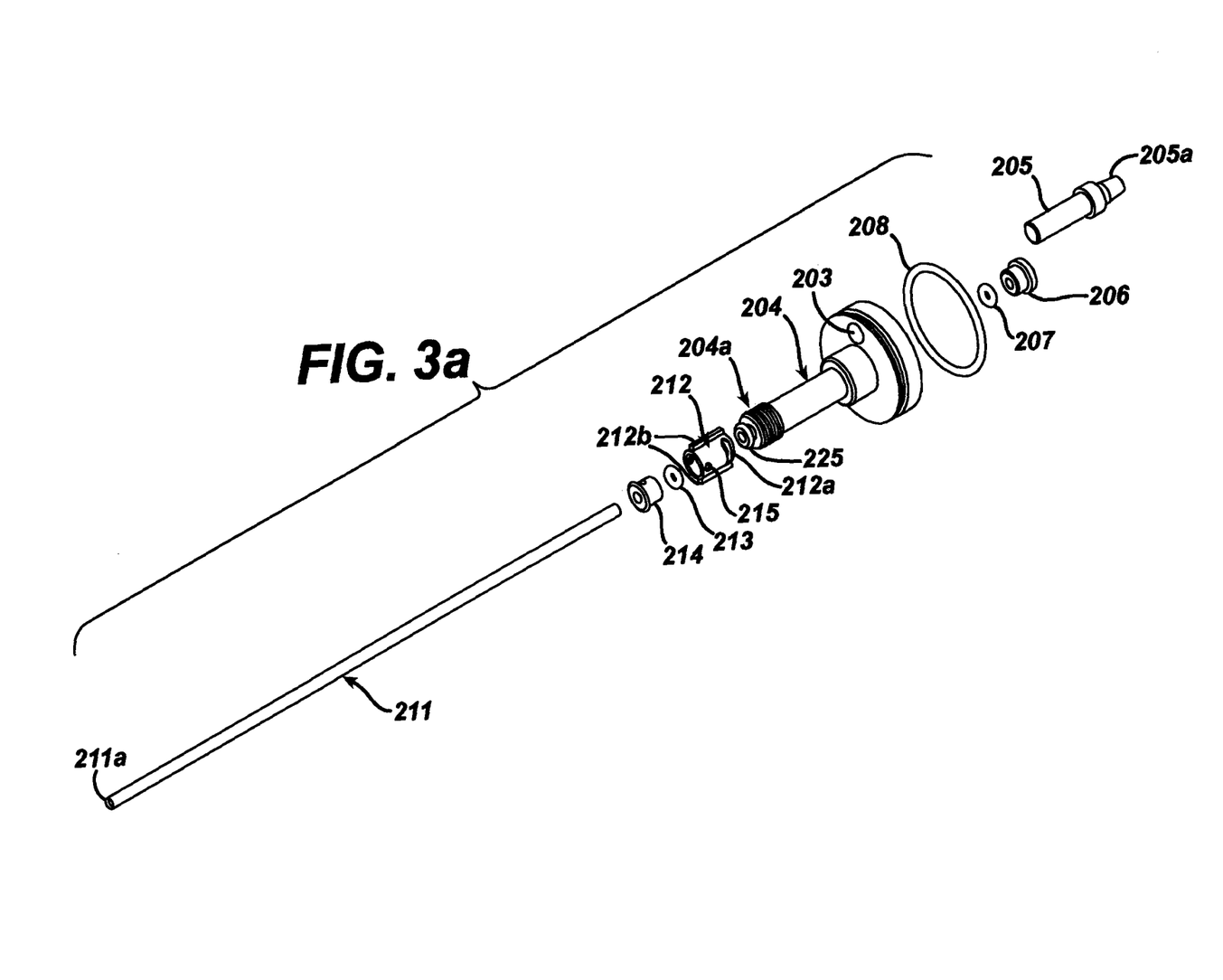
FIG. 3a is an schematic illustration of components of the piston and cutter assembly shown in FIG. 1.
Figure 3B:
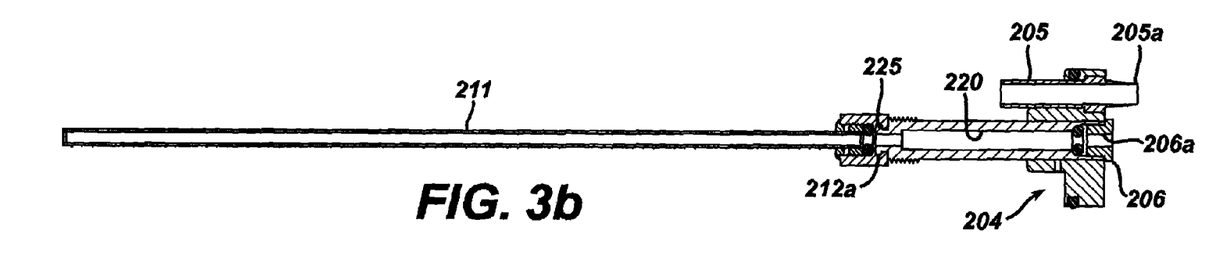
FIG. 3b is a side elevation cross-sectional illustration of the piston and cutter assembly of FIG. 3.

The piston and cutter assembly is shown in FIGS. 3, 3a, and 3b. The piston and cutter assembly 200 includes piston guide 205 which can extend through and be pressed into an axially extending receiving through hole 203 offset from the center of piston 204. Piston guide 205 can be rigidly pressed into receiving through hole 203 in piston 204, or otherwise fixed with respect to the piston 204. Piston guide 205 prevents the piston from rotating axially within tube 420. Piston guide 205 can also provide a low friction seal with guide tube 504 via lip seal feature 205a, which can have a slight interference with guide tube 504.

Still referring to FIGS. 3,3a, and 3b, a piston o-ring plug 206 with central bore 206a can be pressed into a proximal end of a central axial bore 220 in piston (204) to capture knockout o-ring 207. O-ring 207 provides a seal against the outside cylindrical surface of knockout tube 506, when the knockout tube 506 is extended through the central bore 220 of the piston 204.

Piston o-ring seal 208 can be provided in a circumferential groove on the outside surface of the piston 204. O-ring seal 208 provides a vacuum seal between the piston 204 and inside surface of clear thin-walled tube 420 while permitting axial sliding of piston 204 within tube 420.

Still referring to FIGS. 3, 3a, and 3b, the cutter assembly 210 can comprise a cutter clutch o-ring 213, cutter clutch insert 214, cutter clutch housing 212, and cutter 211. Each component can include a central bore or opening to provide a continuous central passageway communicating with the axial bore 220 of the piston and extending from the axial bore 220 of the piston to the distal end of the cutter 211 for receiving the knockout tube 506. Cutter clutch housing 212 is shown having two engagement wings 212b spaced approximately 180 degrees apart around the circumference of the housing 212. The wings 212b can engage with a rotationally driven components to provide rotation of the cutter 211 about its axis, as described more fully below.

The cutter clutch o-ring 213 can be constrained between cutter clutch insert 214 and cutter clutch housing 212. Cutter clutch insert 214 and cutter clutch housing 212 each have central bores through which knockout tube 506 can extend when the device is assembled. The o-ring 213 can provide a seal against the outside cylindrical surface of knockout tube 506 to prevent vacuum leakage.

The elongated hollow tubular cutter 211 has a sharpened distal end 211a, and a proximal end which is inserted into the distal end of the central bore in cutter clutch insert 214. The cutter 211 can be fastened to the cutter clutch insert 214 by a set screw 215 which extends through and engages the cutter clutch housing 212.

A circumferential lip 225 disposed at the distal end of the threaded feature 204a of the piston 204 engages a slot feature 212a in the proximal end of the cutter clutch housing 212. The lip 225 engages the slot feature 212 to couple axial motion of the piston and the cutter assembly, while permitting rotation of the cutter assembly 210 relative to the piston assembly 201. Accordingly, axial motion of the piston causes axial motion of the cutter assembly, but the cutter assembly can be driven rotationally without causing rotation of the piston 204.

Front End Cap Assembly 300

Figures 4, 4A:
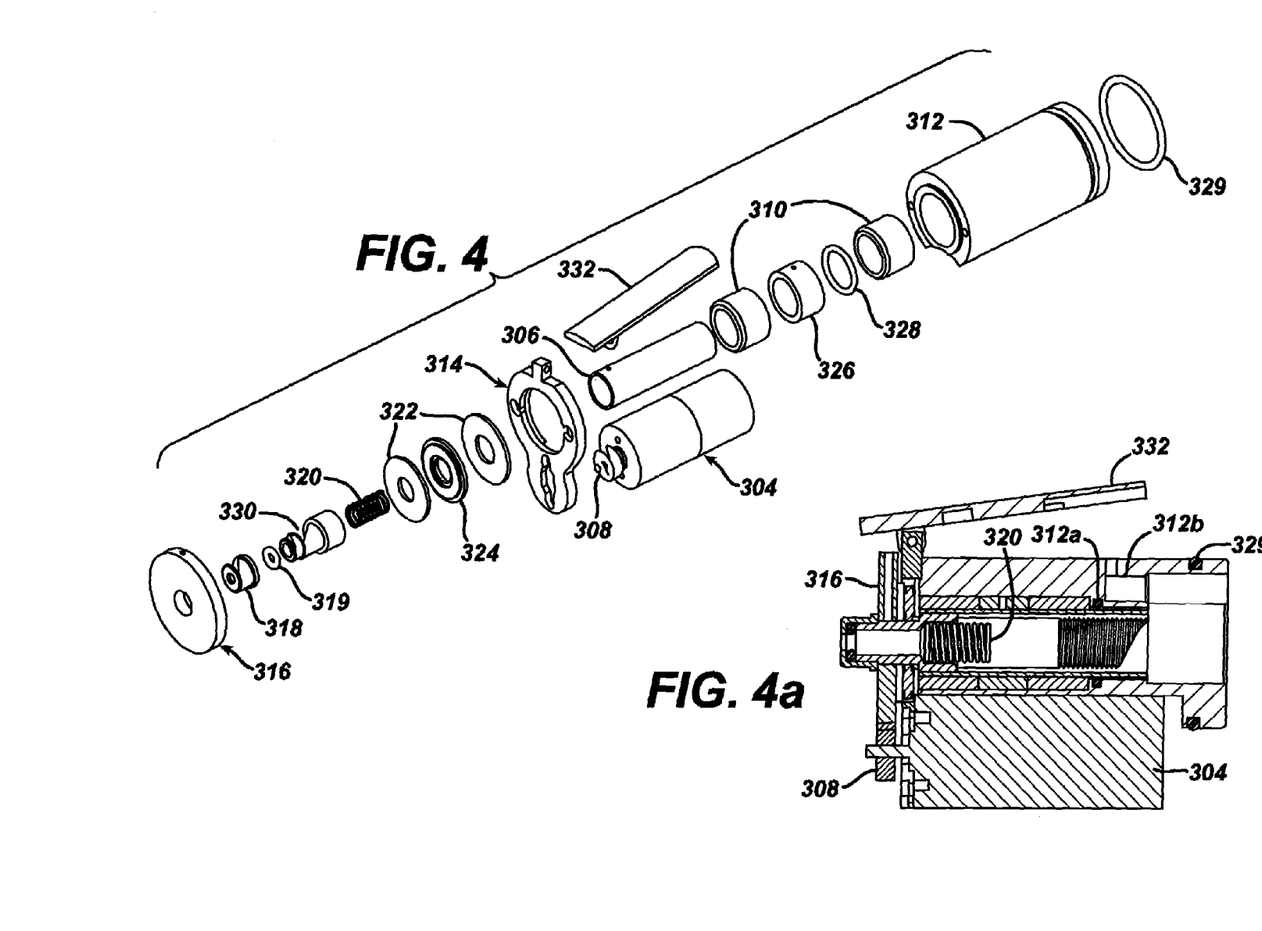
FIG. 4 is an schematic illustration of components of the front end cap assembly shown in FIG. 1.
FIG. 4a is a side elevation cross-sectional illustration of the front end cap assembly.
Figure 4B:
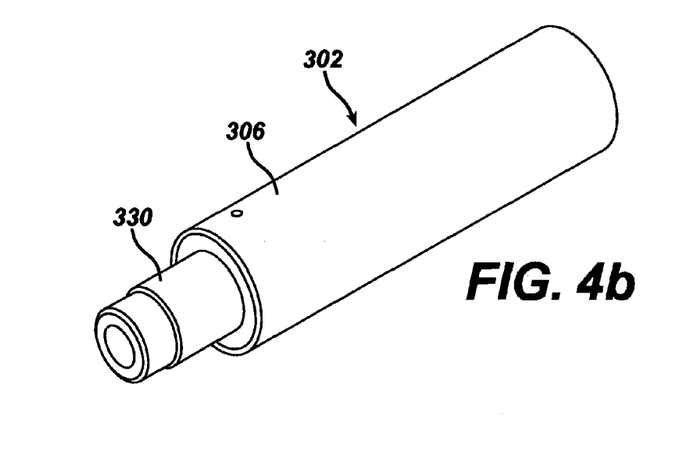
FIG. 4b is a schematic illustration of the journal assembly shown in FIG. 4.

Referring to FIGS. 4 and 4a, the front end cap assembly 300 is shown. Journal cap 330 is rigidly pressed into the distal end of journal 306, which provides journal assembly 302, shown in FIG. 4b. Journal assembly 302 rotates within front end cap assembly 300 as described below.

O-ring housing 318 is rigidly pressed onto journal cap 330, and captures journal cap o-ring 319. Journal cap o-ring 319 seals against the inside circumferential surface of o-ring housing 318 and outside circumferential surface of cutter 211 to prevent vacuum leakage.

Figure 4C:
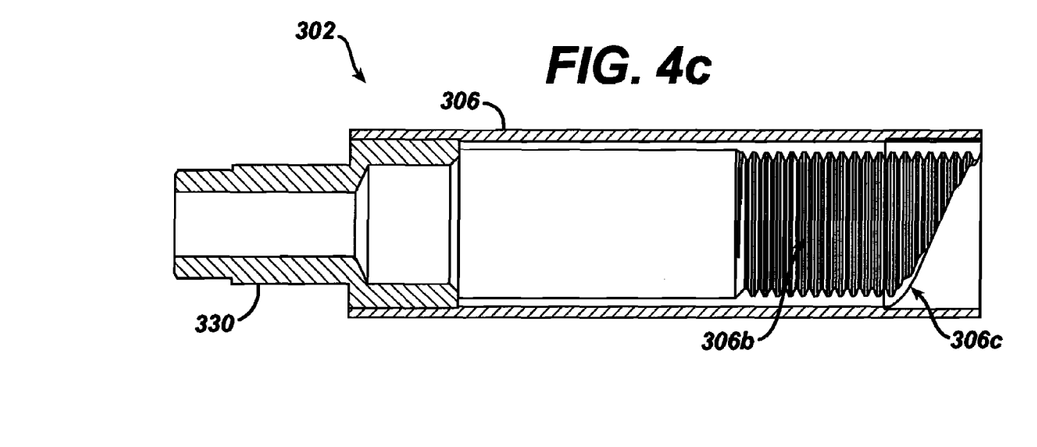
FIG. 4c is a cross-sectional illustration of the journal assembly in FIG. 4b.

Clutch spring 320 is rigidly pressed into journal cap 330, and is used to bias the external piston threaded feature 204a against the distal end of internal journal threaded feature 306b (FIG. 4c). Motor 304 is supported on the front end cap assembly at a position which can be beneath journal assembly 302. A gear train comprising a pinion gear 308 and driven gear 316 conveys rotary motion from the motor 304 to the driven gear 316. The pinion gear 308 can be rigidly mounted to the drive shaft of motor 304. The motor 304 can be supported by a motor mounting bracket 314, which can be attached to journal housing 312, such as by screw fasteners.

Driven gear 316 is mounted to journal cap 330, so that rotation of driven gear 316 results in rotation of journal assembly 302. The driven gear 318 can be supported to bear against thrust washers 322 and needle thrust bearing 324, which in turn are supported to bear against the distal end of the journal housing 312. Accordingly, the journal assembly 302 is constrained from moving axially in the proximal direction. Journal assembly 302 is constrained axially from moving in the in the distal direction by journal thrust ring 326, which can be rigidly mounted to journal assembly 302 by a setscrew or any other appropriate means. Journal 306 is supported radially by proximal and distal needle bearings 310 and rotates within bearings 310. Journal thrust ring 326 bears against the proximal side of the distal needle bearing (310).

Journal o-ring 328 can be lightly pressed into an internal circumferential recess 312a in journal housing 312, thus sealing against journal 306 to prevent vacuum leakage between housing 312 and rotating journal 306. Journal housing o-ring 329 seats in a circumferential exterior groove in the outside surface of journal housing 329, and seals against the inside surface of clear thin-walled tube 420. Finger lever 332 is pivotally attached to motor mounting bracket 314.

Cylinder and Spool Valve Assembly (400)

Figure 5:
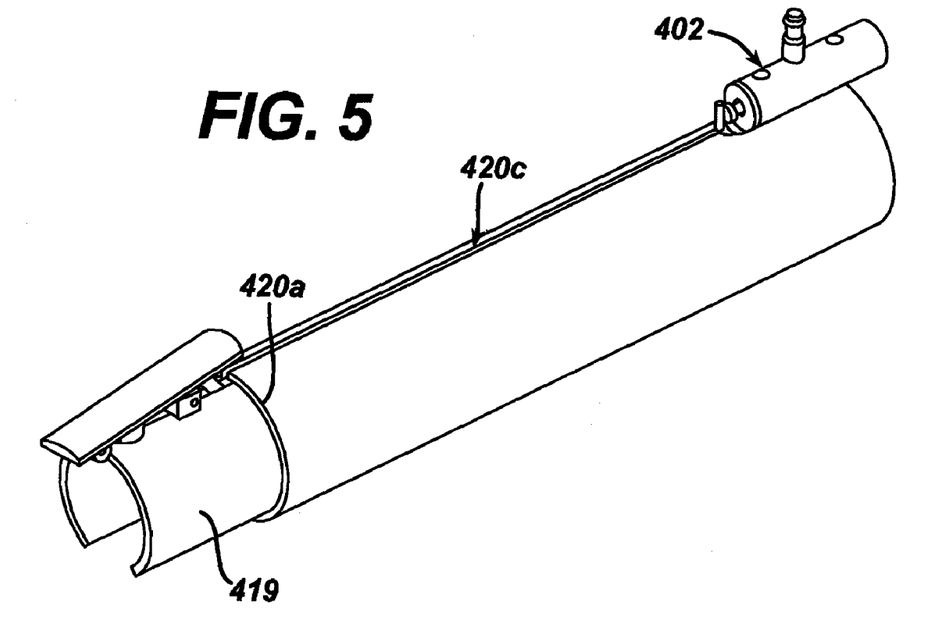
FIG. 5 is a schematic illustration of the cylinder and spool valve assembly shown in FIG. 1.
Figure 5A:
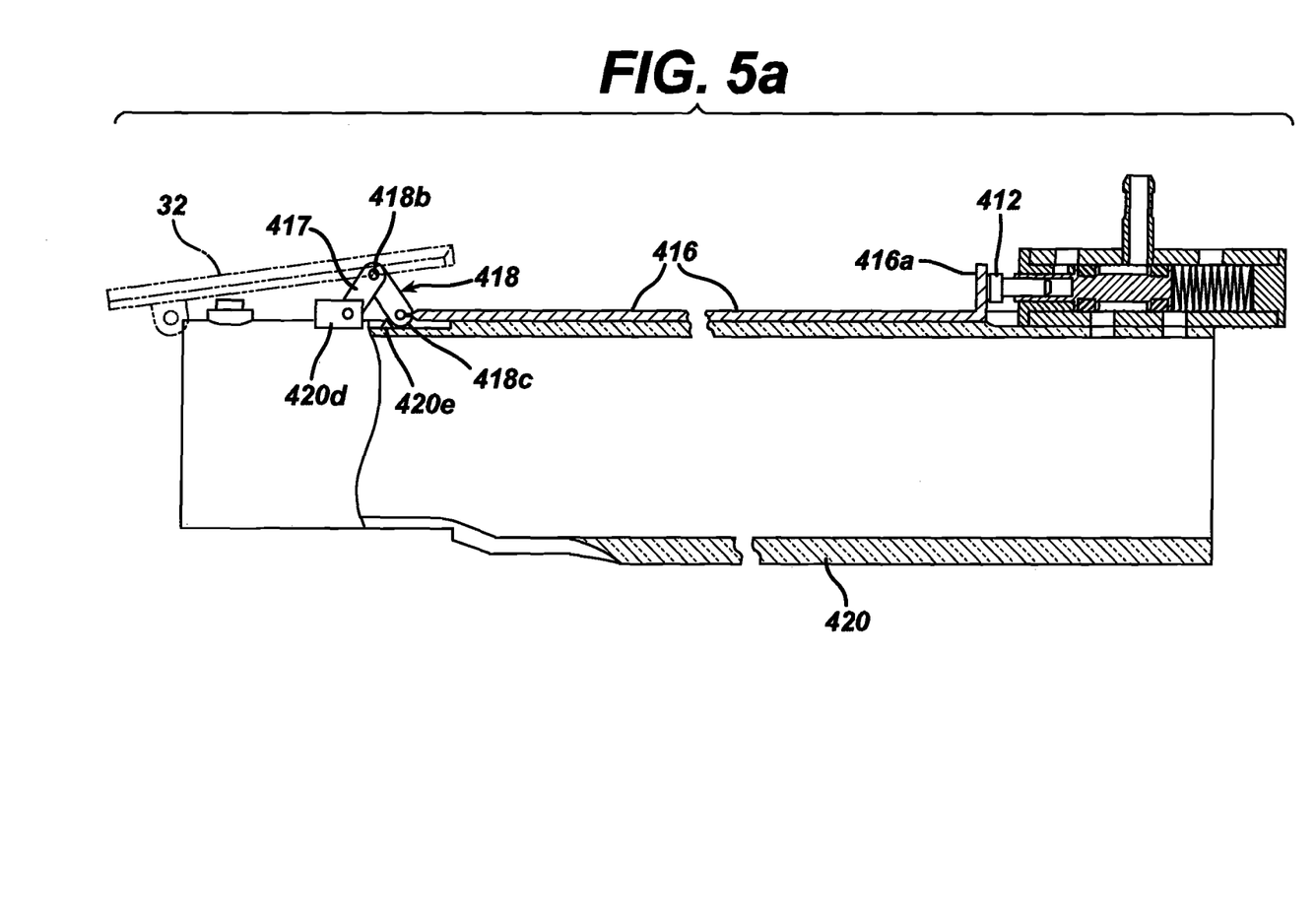
FIG. 5a is a cross-sectional view of the cylinder and spool valve assembly in a released position.
Figure 5B:
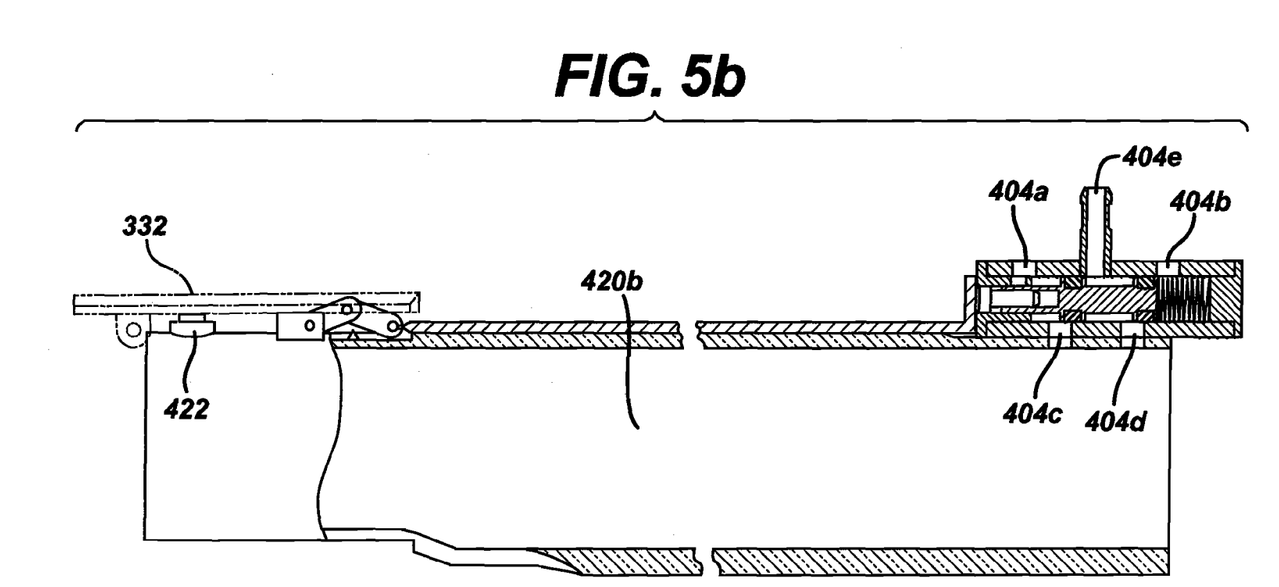
FIG. 5b is a cross-sectional view of the cylinder and spool valve assembly in a depressed posistion.

The cylinder and spool valve assembly is shown in FIGS. 5, 5a, 5b, and 5c. FIG. 5c illustrates components of the spool valve assembly 402. The spool valve assembly 402 can be supported on the proximal end of clear, thin-walled tube 420 to provide a vacuum tight seal between valve body 404 and thin-walled tube 420, with holes 404c and 404d in thin wall tube 420 aligned with ports C and D, respectively, of spool valve assembly 402. The L-bend feature 416a of push wire 416 contacts spool adjustment screw 412. Push wire 416 can be laterally constrained in an axially extending slot feature 420c extending along the length of the top of thin-walled tube 420. The distal end of push wire 416 can be pivotally attached to toggle link 418, which, in turn, is pivotally attached to toggle link 417. Toggle link 417 is pivotally attached to toggle link mounting feature 420d, which can be attached to the top of the thin-walled tube 420.

Referring to FIG. 5c, spool valve assembly 402 includes a spool assembly 410, which has o-rings 414 that lightly seal against the inner cylindrical surface of valve body 404. Spool assembly 410 can be positioned axially, and is constrained at the distal end by valve body front cap 408, and constrained at the proximal end by valve body end cap 406. Spool 410 is biased in the distal direction by spool return spring 409. The distal end of spool assembly 410 receives spool adjustment screw 412 for adjusting clearance with L-bend feature 416a in push wire 416.

When vacuum, from an external source (not shown), is applied to valve external vacuum port 404e in valve body 404, and spool assembly 410 is at rest (or in the distal position shown in FIG. 5a), vacuum occurs at valve port C (hole 404c in tube 420), and atmospheric pressure occurs at valve port D (hole 404d in tube 420). When the spool assembly is activated by depressing lever 332 (position shown in FIG. 5b,) vacuum is applied at valve port D (404d) and atmospheric pressure occurs at valve port C (404c).

Rear End Cap Assembly

Figure 6:
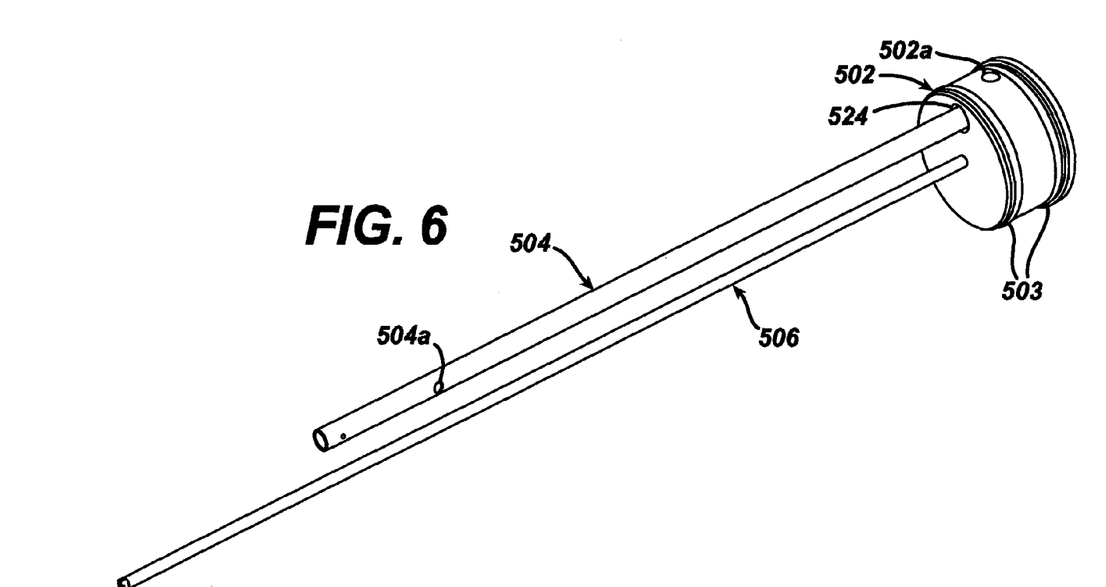
FIG. 6 is a schematic illustration of the rear end cap assembly shown in FIG. 1.
Figure 6A:
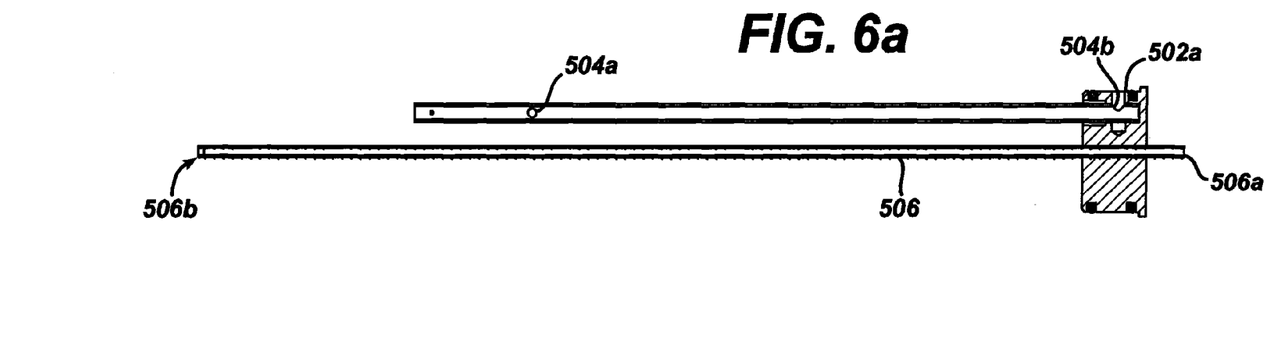
FIG. 6a is a schematic cross-sectional illustration of the rear end cap assembly.

Rear end cap assembly 500 is illustrated in FIGS. 6 and 6a. Assembled to end cap 502 are o-rings 503 which are seated in circumferential grooves in the outside surface of end cap 502. o-rings provide a vacuum tight seal between end cap 502 and the inside circumferential surface of clear, thin-walled tube 420. o-rings 503 also provide a seal between spool valve port D (404d) and end cap vacuum port feature 502a.

End cap vacuum port feature 502a can extend radially inward from the outer surface of end cap 502 to communicate with axially extending cylindrical hole 524 on the distal face of the end cap 502. Hollow guide tube 504 can be pressed into axially extending cylindrical hole 524 in end cap 502 such that a rear guide tube vacuum port feature 504b of the guide tube 504 aligns with end cap vacuum port feature 502a. Accordingly, end cap vacuum port feature 502a can be in flow communication with front guide tube vacuum port 504a through hollow guide tube 504.

Referring to FIG. 6 and FIG. 6a, hollow knockout tube 506 extends from an open proximal end 506a to a distal end 506b. Distal end 506b can have a closed end (or at least partially occluded distal end) with one or more side vacuum holes positioned just proximal of distal end 506b. The proximal end 506a can be connected to a vacuum source (not shown). The knockout tube 506 can extend through a central axial bore in end cap 502, and can extend distally from the distal face of end cap 502. Knockout tube 506 can be rigidly pressed into the central axial bore in end cap 502, and can extend distally a desired distance from the end cap 502 to provide proper core specimen ejection from cutter 211 when cutter 211 is retracted with a severed tissue sample within the distal end of cutter 211.

When end cap assembly is 500 is assembled into the tube 420, the knockout tube 506 extends into the hollow cutter tube 211. When the cutter 211 is fully retracted proximally, the distal end 506b of knockout tube 506 extends just distal of the distal sharpened end 211a of cutter 211, as shown in FIG. 1b, so that the distal end 506b of knockout tube 506 can be used to push tissue samples from cutter tube 211 onto tissue sample surface 112a as the cutter 211 is retracted proximally.

Operation of the Device

The needle 104 can be positioned within a tissue mass, such as by using any suitable imaging method or device. Prior to activating the biopsy device from the position shown in FIG. 1b, continuous vacuum from an external source can be applied in parallel to external vacuum port 404e and to the proximal end 506a of knockout tube 506. The vacuum source for port 404e and 506a can be the same vacuum source communicating with port 108a, or alternatively, separate vacuum sources can be provided. Vacuum applied to the proximal end 506a of tube 506 results in vacuum suction through one or more holes in or near the distal end 506b of tube 506.

To begin the biopsy procedure and activate the biopsy device, the physician depresses and continues to hold finger lever 332. Depressing the lever 332 can serve to: (1) engage a momentary contact switch 422 which starts a motor control sequence and vacuum control sequence; and (2) activate spool valve assembly 402, which causes the cutter 211 to advance rapidly in the distal direction.

Depressing lever 332 pushes downward on toggle link joint feature 418b. The downward force on toggle link joint feature 418b causes toggle link end feature 418c to translate proximally, because toggle link 417 is pivotally attached to the thin-wall tube 420 at toggle link mounting feature 420d, and toggle link end feature 418c is constrained to travel in the horizontal direction only (along the axis of tube 420). The toggle link assembly collapses downward, which provides tactile feedback to the physician that the device has been activated. Limit stop feature (420e) or other upstanding feature can prevent toggle links 417 and 418 from traveling over-center and locking.

Push wire (416) is pivotally attached at toggle link end feature 418c, and translates in the proximal direction upon depression of lever 332. Push wire L-bend feature 416a presses against the end of spool assembly 410, which is biased in the distal direction by return spring 409. The spool valve is thereby activated and vacuum is applied to valve body port d and hole 404d in tube 420.

Figure 4D:
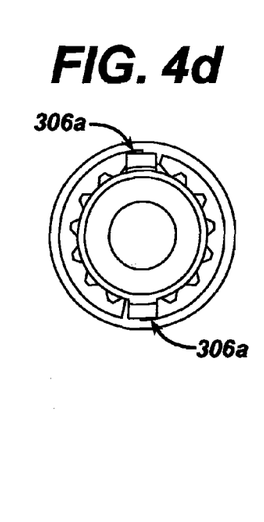
FIG. 4d is an end view of the journal assembly in FIG. 4c.

Vacuum through valve body port d and hole 404d evacuates the distal side of piston assembly 201 through end cap vacuum port feature 502a, rear guide tube vacuum port feature 504b, guide tube 504, and front guide tube vacuum port feature 504a. This causes the piston and cutter assembly 200 to advance rapidly (move distally), causing clutch engagement wings 212b to enter two diametrically opposed journal helical engagement ramp features 306c in journal 306 (FIGS. 4c and 4d). The ramp features 306c, in turn, cause cutter clutch engagement wings 212b to engage two diametrically opposed journal channel slot features 306a, thereby releasably coupling rotation of cutter assembly 210 with rotation of the journal assembly 302. With the cutter assembly 210 releasably keyed to rotate with journal assembly 302, cutter assembly 210 and cutter 211 will rotate with journal assembly 302 upon journal assembly 302 being rotationally driven, as described below.

Figure 7:
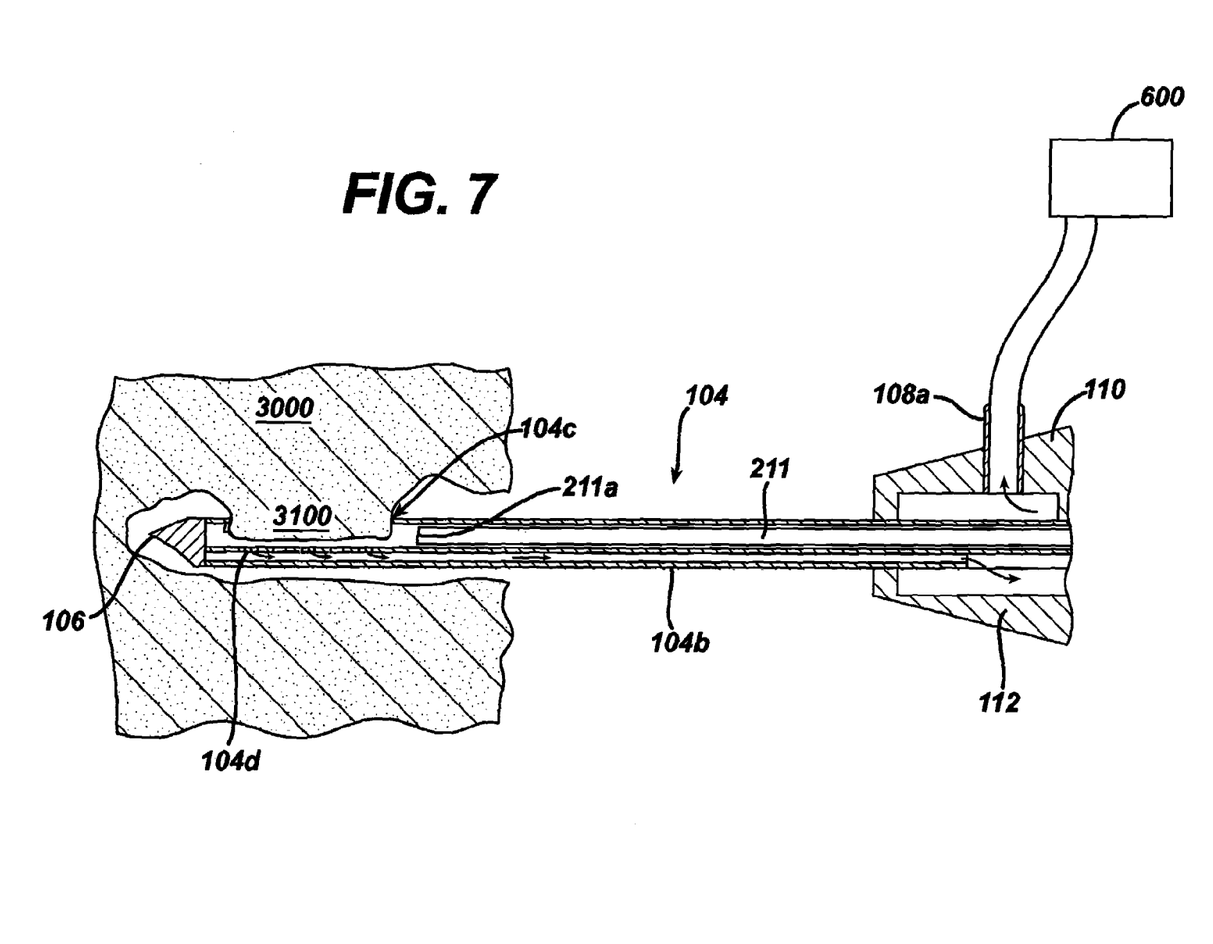
FIG. 7 is a schematic cross-sectional illustration showing the cutter advanced by the piston mechanism to a first position within the cutter lumen of the needle, the first position being just proximal of the lateral tissue receiving port, and also showing tissue drawn into the lateral tissue receiving port by vacuum conveyed through a lower vacuum lumen in the needle.

Piston and cutter assembly 200 will stop advancing distally due to force exerted by piston 204 when the distal end of piston thread feature 204a contacts the proximal side of journal thread feature 306b. The assembly can be configured such that when the piston and cutter assembly 200 stop advancing due to the force exerted by the piston, the sharpened distal end 211a of the cutter 211 is positioned at a first position just proximal of the port 104c in the hollow needle 104. This position illustrated schematically in FIG. 7. At this point, the vacuum at valve port 404d is turned off in order to reduce friction forces when the threads begin to rotate. This vacuum sequence can be provided via a mechanical or digital timer or switch. For instance, vacuum control software can be employed to monitor and/or control the vacuum sequence. Simultaneously, vacuum at needle inlet port 108a can be provided, to provide vacuum suction at tissue receiving port 104c via vacuum lumen 104b and vacuum holes 104d. This lateral vacuum, combined with preexisting axial vacuum through knockout tube 506 (which is communicated through the inside of hollow cutter 211 which has been advanced by the piston distal travel such that cutter distal end 211a is just proximal of port 104c) draws tissue laterally into lateral port 104c and axially into upper lumen 104a. Referring to FIG. 7, the needle 104 is shown positioned in a tissue mass 3000, with a portion 3100 of tissue mass 3000 drawn into port 104c by vacuum provided through interlumen vacuum holes 104d.

After the vacuum at valve port 404d is turned off, motor 304 is controlled by a suitable mechanical or digital control sequence to rotate journal assembly 302 a predetermined number of revolutions corresponding to a desired axial advancement of the cutter 211 distal end 211a past the tissue receiving port 104c. The journal threads 306b engage the piston threads 204a, and advance the piston and cutter assembly 200 in lead screw fashion distally a predetermined distance to a second position distal of port 104c to sever tissue 3100 from mass 3000. At the same time cutter 211 is translating, the cutter assembly 210 rotates with the journal assembly 302 due to the rotational coupling provided by the wings 212b. Thus, rotation of journal assembly 302 causes the hollow cutter tube 211 to advance forward and rotate, while the piston advances forward without rotation.

As the cutter assembly (210) advances forward and rotates, the sharp distal end 211a of the cutter 211 cuts the tissue 3100 drawn into the lateral port 104c as the cutter distal end 211 advances from the proximal end of the port 104c to a second position distal of the distal end of the port 104c. At the end of the cutting the stroke, the fully cut tissue specimen, or core specimen, resides in the distal end of cutter 211.

Just as cutter assembly 210 reaches the end of the stroke, piston threaded feature 204a travels completely through journal threaded feature 306b ("runs off" threaded feature 306b), thereby completely disengaging the threads. This disengagement causes cutter assembly 210 to stop translating. However, cutter assembly 210 can continue to rotate due to rotation of journal 306 by motor 304 and engagement of wings 212b in journal channel slot features 306a. Return spring 409, in front cap assembly 300, will cause piston and cutter assembly 200 to be biased proximally against journal threaded feature 306b, thereby insuring re-engagement of threads 204a when the direction of journal rotation is reversed (such as by reversing the rotation of the motor).

If desired, the position of the cutter can be tracked directly or indirectly for use in monitoring or controlling the operation of the device. For example, one or more encoders can be used to track the number of rotations of the motor main shaft, or to otherwise track the number of revolutions made by the motor. Additional encoders, hall effect switches, or other suitable devices and transducers can be used to monitor the position of the cutter if desired.

After the threads 204a disengage from 306b, and the cutter distal end 211a is at its distal most extent of travel, the cutter assembly 200 can be rotated for a predetermined period of time or predetermined number of rotations to insure that the core specimen is fully cut from the surrounding tissue. A mechanical switch, digital timer, vacuum control software, or other suitable control method can then be used to turn off the vacuum to needle lateral port 104c so that atmospheric pressure is present in the cutter lumen 104a at the side port 104c. This will eliminate vacuum force on the distal side of the severed tissue core, thus facilitating removal of the core specimen through needle upper lumen 104a.

At this point in the operation of the device, the physician can continue to depress and hold finger lever 332. After the tissue sample has been severed the rotation of cutter assembly 210 can be stopped, and atmospheric pressure can be provided at needle lateral port 104c. Atmospheric pressure can also be provided at spool valve external vacuum port feature 404e, and therefore no vacuum force on piston assembly 201. Vacuum can be maintained at the proximal end of the core specimen, within cutter assembly 210, via knockout tube 506, if desired.

To retract the core specimen, the physician can release finger lever 332. Releasing the lever 332 can: (1) disable momentary contact switch 422, which can used to provide a signal to the motor and vacuum control software or other control means to initiate a reversing sequence; and (2) allow toggle link joint feature 418b to move upward, which allows spool assembly 410 to return to the distal position.

Upon release of lever 332, motor 304 can be operated to run in reverse a predetermined number of revolutions, simultaneously rotating and retracting cutter assembly 210, until piston threaded feature 204a disengages from the proximal end of journal threaded feature 306b, so that cutter 211 is positioned at the first position just proximal of the port 104c. After this occurs, rotation of motor 304 can be stopped (and motor control software can be reset if digital control is used), and vacuum can be applied to spool valve external vacuum port 404e, to provide vacuum on the proximal side of piston assembly 201, with spool assembly 410 in the distal position. Vacuum provided on the proximal side of piston assembly 201 causes piston and cutter assembly 200 to retract rapidly to the fully proximal position shown in FIG. 1b, such that cutter 211 is withdrawn from needle upper cutter lumen 104a.

As piston and cutter assembly 200 is retracted, the air inside cutter 211 is evacuated via the vacuum applied to cutter 211 through knockout tube 506. This insures that the core specimen remains in a fixed position within the distal end of cutter 211 as piston and cutter assembly 200 accelerates rearward (proximally). At the end of the stroke, the proximal end of the tissue core specimen contacts the closed or partially closed distal end 506b of knockout tube 506, thereby ejecting the core specimen onto specimen tray surface 112a.

The present invention provides a two stage, sequenced cutter advance. The first stage of the cutter advance is provided using a first mechanism, such as a fluid (gas or liquid) mechanism, while the second stage of cutter advance is provided using a second mechanism, such as mechanical engagement of threaded components. The first mechanism can comprise a pneumatically driven piston used to provide a relatively rapid cutter advance to a first position just proximal of the tissue receiving port, while the mechanical advancement using mechanical thread engagement can provide a relatively less rapid cutter advance rate for effective tissue cutting. The mechanical engagement of the screw threads can provide mechanical advantage for cutting the core specimen at a controlled, predetermined rate during rotation of the cutter. The cutter assembly is coupled to the piston assembly for translation, but can rotate relative to the piston assembly when releasably engaged with the rotating journal. Additionally, the physician can control the spool valve directly, using a finger lever, so that an electronically operated solenoid valve is not required. Such a finger lever in the embodiment provided is also intuitive to operate as when the finger lever is depressed, the cutter can be advanced distally, and when the finger lever is released, the cutter can be retracted.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. For instance, a pneumatic piston has been illustrated, but it will be understood that other fluid actuators, including hydraulic actuators employing a liquid could be employed. While the mechanical drive used to advance and rotate the cutter during tissue severing employs an motor, gear train, and releasably engaging threading members, other drive mechanisms can be employed. Alternatively, the cutter could be translated without rotation if desired. Moreover, the structure of each element associated with the present invention can be alternatively described as a means for providing the function performed by the element. Accordingly, it is intended that the invention be limited only by the spirit and scope of the appended claims.

What is claimed is:

1. A biopsy device comprising:
a hollow biopsy needle having a lateral tissue receiving port;
a hollow cutter advancable within the biopsy needle, the cutter having a distal end;
a first mechanism for advancing the distal end of the cutter to a position proximal of the lateral tissue receiving port; wherein the first mechanism employs pneumatics; and
a second mechanism for advancing the distal end of the cutter distal of said position proximal of the lateral tissue receiving port, wherein the second mechanism does not employ pneumatics.

2. The biopsy device of claim 1 wherein the first mechanism employs a pressure differential for advancing the cutter.

3. The biopsy device of claim 1 wherein said second mechanism rotates and advances said cutter.

4. The biopsy device of claim 1 wherein the first mechanism advances the cutter at first rate, and wherein the second mechanism advances the cutter at a second rate.

5. The biopsy device of claim 4 wherein the first rate is different from the second rate.

6. The biopsy device of claim 4 wherein the first rate is greater than the second rate.

7. The biopsy device of claim 1 wherein at least one of the first and second mechanisms comprises a piston.

8. The biopsy device of claim 7 wherein the piston is non-rotating.

9. The biopsy device of claim 1 wherein the first mechanism advances the cutter without rotation of the cutter, and wherein the second mechanism advances and rotates the cutter.

10. The biopsy device of claim 1 wherein the second mechanism advances the cutter from a position proximal of the tissue receiving port to a position distal of the tissue receiving port.

11. The biopsy device of claim 10, wherein the second mechanism is further operable to retract the cutter from the position distal of the tissue receiving port to the position proximal of the tissue receiving port.

12. The biopsy device of claim 1, wherein the second mechanism is operable to simultaneously advance and rotate the cutter.

13. The biopsy device of claim 12, wherein the first mechanism is not operable to rotate the cutter.

14. A biopsy device comprising:
- a hollow biopsy needle having a lateral tissue receiving port;
- a hollow cutter advancable within the biopsy needle, the hollow cutter having an open distal end;
- a first mechanism for advancing the distal end of the cutter to a position proximal of the lateral tissue receiving port, wherein the first mechanism is not operable to rotate the cutter; and
- a second mechanism for advancing the distal end of the cutter to a position distal of the lateral tissue receiving port, wherein the second mechanism is operable to simultaneously advance and rotate the cutter.

15. The biopsy device of claim 14, wherein the first mechanism has at least one component that is not in the second mechanism.

16. The biopsy device of claim 14, wherein the second mechanism does not employ pneumatics.

17. The biopsy device of claim 14, wherein the first mechanism comprises a piston.

18. The biopsy device of claim 17, wherein the second mechanism comprises threaded components engageable with one another.

19. A biopsy device comprising:
- a hollow biopsy needle having a lateral tissue receiving port;
- a hollow cutter having a distal end advancable within the biopsy needle;
- a fluid driven piston operatively associated with the cutter for advancing the distal end of the cutter to a position proximal of the lateral tissue receiving port; and
- a non-pneumatic mechanism operatively associated with the cutter for advancing the distal end of the cutter from the position proximal of the lateral tissue receiving port to a position distal of the lateral tissue receiving port.

* * * * *